United States Patent [19]

Johnsson et al.

[11] Patent Number: 5,503,977
[45] Date of Patent: Apr. 2, 1996

[54] SPLIT UBIQUITIN PROTEIN SENSOR

[75] Inventors: Nils Johnsson; Alexander Varshavsky, both of Pasadena, Calif.

[73] Assignee: California Institute of Technology, Pasadena, Calif.

[21] Appl. No.: 232,815

[22] Filed: Apr. 22, 1994

[51] Int. Cl.$^6$ ............................. C07K 19/00; C12Q 1/68; C12N 15/62; C12N 15/63
[52] U.S. Cl. ..................... 435/6; 530/350; 530/403; 435/69.7; 435/172.3; 435/320.1; 536/23.4; 935/10; 935/76; 935/79; 935/80
[58] Field of Search ................................. 530/350, 403; 435/6, 172.3, 320.1, 69.7; 536/23.4; 935/10, 79, 80, 76

[56] References Cited

U.S. PATENT DOCUMENTS 5,283,173  2/1994  Fields et al. ................... 435/5

OTHER PUBLICATIONS

Cox et al. (1993). Dissecting the structure of a partially folded protein . . . *J. Mol. Biol.* 234, 483–492.
Guarente (1993). Strategies for the identification of interacting proteins. *Proc. Natl. Acad. Sci. USA* 90, 1639–1641.
Germino et al. (1993). Screening for in vivo protein–protein interactions. *Proc. Natl. Acad. Sci. USA* 90, 933–937.
Blackwood and Eisenman (1991). MAX: A helix–loop–heliz zipper protein that forms a sequence–specific DNA–binding complex with myc. *Science* 251, 1211–1217.
DeFeo–Jones et al. (1991(). Cloning of cDNAs for cellular proteins that bind to the retinoblastoma gene product. *Nature* 352, 251–254.
Blanar and Rutter (1992). Interaction cloning: identification of a helix–loop–helix zipper protein that interacts with c–Fos. *Science* 256, 1014–1018.
Fields and Song (1989). A novel genetic system to detect protein–protein interactions. *Nature* 340, 245–246.
Chien et al. (1991). The two–hybrid system: A method to identify and clone genes for proteins that interact with a protein of interest. *Proc. Natl. Acad. Sci. USA* 88, 9578–9582.
Stockman et al. (1993). Heternuclear three–dimensional NMR spectroscopy of a partially denatured protein: The A–state of human ubiquitin. *J. Biomolecular NMR* 3, 285–296.

Primary Examiner—Robert A. Wax
Assistant Examiner—Rebecca Prouty
Attorney, Agent, or Firm—Farrell Kevin M.

[57] ABSTRACT

Disclosed are novel compositions and methods useful for studying interactions between proteins. An N-terminal subdomain and a C-terminal subdomain of ubiquitin are linked to a pair of proteins or peptides to be examined for their ability to interact. When contacted with one another, a quasi-native ubiquitin moiety is reconstituted provided that the protein or peptide pair do, in fact, interact (bind) with one another. The quasi-native ubiquitin moiety is recognized and cleaved by ubiquitin-specific proteases after the last residue of ubiquitin. The cleavage at the quasi-native ubiquitin moiety within a linear protein fusion is the indication of interaction between the protein or peptide pair.

16 Claims, 3 Drawing Sheets

SPLIT UBIQUITIN PROTEIN SENSOR

GOVERNMENT SUPPORT

Work described herein was supported by grants from the United States government and the government has rights to the invention described herein.

BACKGROUND OF THE INVENTION

Multiprotein complexes mediate the bulk of biological processes. A crucial part of our understanding of these processes is therefore based on knowing which proteins interact with a protein of interest. This knowledge is extensive for oligomeric proteins whose subunit interactions are strong enough to withstand in vitro conditions. However, many oligomeric complexes, while relevant physiologically, are either transient, intrinsically unstable, or are destabilized upon dilution, depletion of cofactors and other perturbations that accompany a transition from in vivo to in vitro conditions. In part as a result of this difficulty, the existing knowledge encompasses but a small fraction of the actually occuring, physiologically relevant protein-protein interactions even among the best understood organisms. Moreover, even for proteins whose in vivo protein ligands are partly known, this knowledge is often of a qualitative kind; it rarely includes the actual affinities, let alone kinetic aspects of an in vivo interaction. Limitations of the existing in vivo methods are a major reason for this impasse.

Assays for in vivo protein interactions include crosslinking of interacting proteins with a cell-penetrating agent such as formaldehyde, and use of fluorescence resonance energy transfer to follow the interactions of dye-coupled proteins microinjected into living cells. Genetic analyses of in vivo protein interactions include searches for extragenic suppressor mutations or synthetic lethal mutations, which occur in genes whose products are at least functionally (and often physically) associated with a gene product of interest. A more recent approach, the two-hybrid technique, is based on expressing one test protein as a fusion to a DNA-binding domain of a transcriptional activator, and expressing another test protein as a fusion to a transcriptional activation domain. If the test proteins interact in vivo, a transcriptional activator is reconstituted, resulting in the induction of a reporter gene.

The repertoire of existing assays for in vivo protein interactions, while expanding, is deficient in that significant questions cannot be answered due to technical limitations. New techniques which fill these experimental voids would represent important steps forward in the art.

SUMMARY OF THE INVENTION

The present invention relates to compositions and methods useful for studying interactions between proteins. A composition of the invention is a fusion protein comprising an N-terminal subdomain of ubiquitin, fused to a non-ubiquitin protein or peptide. A second composition of the invention is a fusion protein comprising a C-terminal subdomain of ubiquitin, fused to the N-terminus of a non-ubiquitin protein or peptide. When contacted with one another, provided that the non-ubiquitin proteins or peptides interact (bind) with one another, the N- and C-terminal ubiquitin subdomains associate to reconstitute a quasi-native ubiquitin moiety which is recognized and cleaved by ubiquitin-specific proteases. As discussed in greater detail below, either the N-terminal subdomain of ubiquitin or the C-terminal subdomain of ubiquitin must be mutationally altered to reduce the ability of the ubiquitin subdomains to reconstitute a quasi-native ubiquitin moiety.

Other compositions of the present invention include DNA-based expression vectors encoding fusion proteins of the type described in the preceding paragraph. In addition, DNA-based expression vectors containing an expression cassette containing randomly cleaved DNA from an organism fused to either the N- or C-terminal ubiquitin subdomains are disclosed. Such constructs are useful for expression library screening.

Compositions of the type described above are useful in methods for studying protein/protein interactions. Fusion proteins containing an N-terminal ubiquitin subdomain are contacted with fusion proteins containing a C-terminal ubiquitin subdomain. Provided that protein or peptide components other than the ubiquitin components interact with one another, the "effective" (local) concentration of the N- and C-terminal ubiquitin subdomains is increased, thereby promoting reconstitution of a quasi-native ubiquitin moiety, which is subsequently cleaved by ubiquitin-specific proteases. A number of assay formats, including in vivo and in vitro formats, are described herein.

(A) A newly formed ubiquitin (Ub) moiety bearing an insertion (wavy thin line) between its N-terminal (semicircle denoted as "$N_{ub}$";) and C-terminal (semicircle denoted as "$C_{ub}$";) "halves", and linked to a reporter protein (oval denoted as "Re";). The insertion did not detectably interfere with the Ub folding, which was required for the rapid in vivo cleavage of the fusion by Ub-specific proteases (UBPs; lightning arrow), yielding the free reporter.

Figure 2:
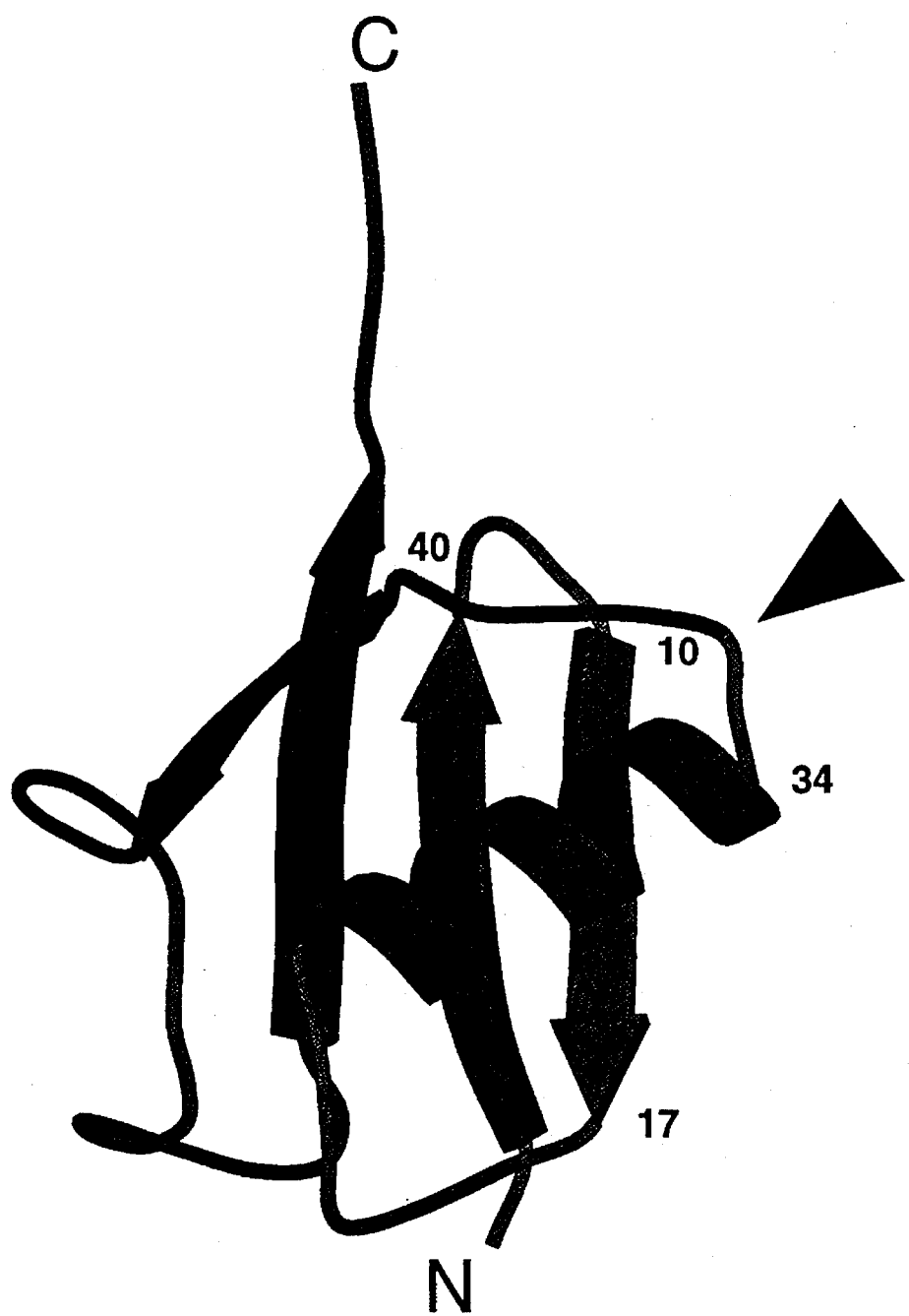

(B) The result in A suggested that the $N_{ub}$ and $C_{ub}$ halves of Ub can be viewed as its distinct subdomains (FIG. 2). When these subdomains were coexpressed as separate fragments, with $C_{ub}$ still linked to the reporter, significant in vivo reconstitution of a quasi-native (recognizable by UBPs) Ub moiety was observed.

(C) In vivo reconstitution of Ub from its separate, coexpressed fragments did not occur with an altered $N_{ub}$ fragment, denoted as $N_{ub}^m$ (mutant), that bore a single-residue replacement at position 13. Conformational destabilization of $N_{ub}^m$ relative to its wild-type counterpart $N_{ub}$ is indicated by the altered shape of the $N_{ub}^m$ subdomain. A cross over the arrow indicates the absence of Ub reconstitution.

(D) Ubiquitin-based Split-Protein Sensor (USPS). $N_{ub}^m$, a mutationally altered fragment of Ub that failed to reconstitute Ub in the presence of $C_{ub}$, could still do so if the two Ub fragments were linked to polypeptides $P_1$ and $P_2$ (two ovals) that interacted in vivo. This interaction increased the effective (local) concentration of Ub fragments, and therefore increased the probability of $N_{ub}^m$ and $C_{ub}$ associating to form a quasi-native Ub moiety. This event was detected by the irreversible, diagnostic, UBP-mediated cleavage after the last residue of Ub in $C_{ub}$, yielding the free reporter. Reduced conformational stability of Ub that has been reconstituted with $N_{ub}^m$ instead of $N_{ub}$ is denoted by a gap between the "interacting" surfaces of Ub subdomains.

Figure 1:
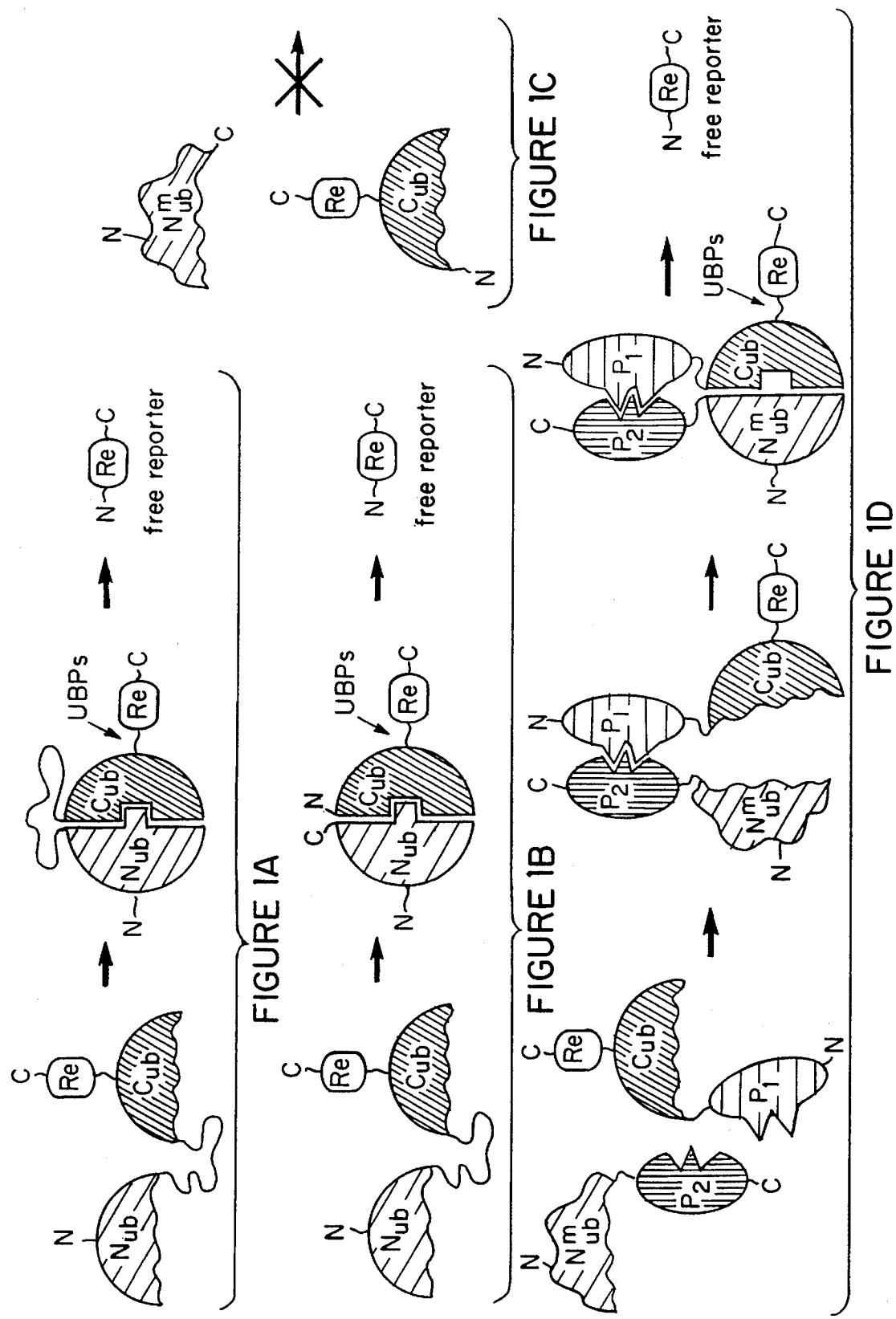
FIGS. 1(A–D) is a diagram representing split ubiquitin as a proximity sensor in vivo.
Figure 3:
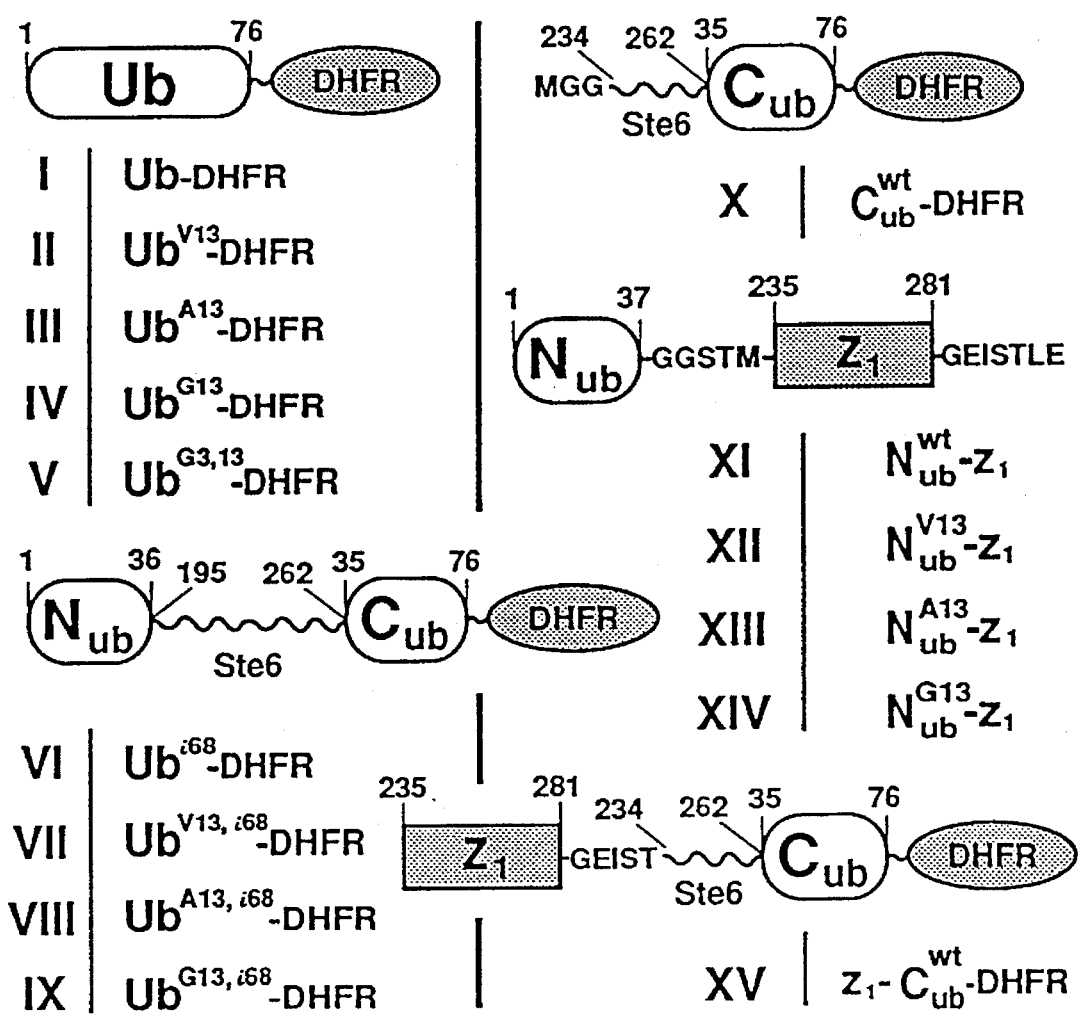

FIG. 2 is a ribbon diagram of Ub with the two subdomains identified in the present work, encompassing residues ~1 to ~37 and ~38 to ~76. A black triangle denotes the site of a 68-residue insertion between the subdomains (FIGS. 1A and 3-VI). Some of the residue numbers are indicated Ile$^{13}$ the site of mutations analyzed in this work (FIG. 3), is in the second strand of the β-sheet, where it interacts with the hydrophobic face of the α-helix.

FIG. 3 is a diagram showing the fusion constructs of the present invention. These fusions contained some of the following elements: (i) a Ub moiety, either wild-type (construct I) or bearing single-residue replacements at position 13 (constructs II–IV), or at positions 3 and 13 (construct V). (ii) A Ub moiety containing the 68-residue insertion (denoted as "Ste6" in the diagram) derived from the cytosolic region of *S. cerevisiae* Ste6 between its transmembrane segments 4 and 5. The insertion was positioned after residue 36 of Ub (construct VI). (iii) A Ub moiety bearing both the above insertion and a single-residue replacement at position 13 (constructs VII–IX). (iv) A C-terminal fragment of Ub ($C_{ub}$, residues 35–76) bearing the 32-residue, Ste6-derived sequence at its N-terminus (construct X). (v) $C_{ub}$ whose N-terminus was extended, via the linker sequence Gly-Glu-Ile-Ser-Thr (SEQ ID NO. 5), with the 47-residue homodimerization motif ("leucine zipper" or $z_1$) of *S. cerevisiae* Gcn4 (residues 235–281 of Gcn4) (construct XV). (vi) An N-terminal fragment of Ub ($N_{ub}$, residues 1–37) bearing the wild-type Ub sequence or a single-residue replacement at position 13, and a C-terminal extension containing the linker sequence Gly-Gly-Ser-Thr-Met (SEQ ID NO. 3) followed by the $z_1$ leucine zipper of Gcn4 (constructs XI–XIV). (vii) Mouse dihydrofolate reductase (DHFR) bearing a C-terminal ha epitope (denoted as "DHFR" in the diagram and as "dha" in the text). The explicitly indicated amino acid sequences are in single-letter abbreviations. All constructs were expressed from the induced $P_{CUP1}$ promoter.

DETAILED DESCRIPTION OF THE INVENTION

Ubiquitin (Ub) is a 76-residue, single-domain protein (FIG. 2) whose covalent coupling to other proteins yields branched Ub-protein conjugates and plays a role in a number of cellular processes, primarily through routes that involve protein degradation. Unlike the branched Ub conjugates, which are formed posttranslationally, linear Ub adducts are the translational products of natural or engineered Ub fusions. It has been shown that, in eukaryotes, newly formed Ub fusions are rapidly cleaved at the Ub-polypeptide junction by Ub-specific proteases (UBPs). In the yeast Saccharomyces cerevisiae, there are at least five species of UBP. Recent work has shown that the cleavage of a Ub fusion by UBPs requires the folded conformation of Ub, because little or no cleavage is observed with fusions whose Ub moiety was conformationally destabilized by single-residue replacements or a deletion distant from the site of cleavage by UBPs.

The present invention is based on the discovery that a fusion protein comprising a ubiquitin subdomain is useful, for example, in a method for studying the interactions between proteins and/or peptides. For convenience, the term "protein(s)" will be used throughout the description of the present invention in the context of studying protein and/or peptide interaction as a shorthand expression for "protein(s) or peptide(s)".

Briefly, it has been demonstrated that an N-terminal ubiquitin subdomain and a C-terminal ubiquitin subdomain, the latter bearing a reporter extension at its C-terminus, when coexpressed in the same cell by recombinant DNA techniques as distinct entities, have the ability to associate, reconstituting a ubiquitin molecule which is recognized, and cleaved, by ubiquitin-specific processing proteases which are present in all eukaryotic cells. This reconstituted ubiquitin molecule which is recognized by ubiquitin-specific proteases is referred to herein as a quasi-native ubiquitin moiety. As disclosed herein, ubiquitin-specific proteases recognize the folded conformation of ubiquitin. Remarkably, ubiquitin-specific proteases retained their cleavage activity and specificity of recognition of the ubiquitin moiety that had been reconstituted from two unlinked ubiquitin subdomains.

Ubiquitin is a 76-residue, single-domain protein comprising two subdomains which are relevant to the present invention—the N-terminal subdomain and the C-terminal subdomain. The ubiquitin protein has been studied extensively and the DNA sequence encoding ubiquitin has been published (Özkaynak et al., *EMBO J.* 6:1429 (1987)) (SEQ ID NO. 1). The N-terminal subdomain, as referred to herein, is that portion of the native ubiquitin molecule which folds into the only α-helix of ubiquitin interacting with two β-strands. Generally speaking, this subdomain comprises amino acid residues from about residue number 1 to about residue number 36.

The C-terminal subdomain of ubiquitin, as referred to herein, is that portion of the ubiquitin which is not a portion of the N-terminal subdomain defined in the preceding paragraph. Generally speaking, this subdomain comprises amino acid residues from about 37 to about 76. It should be recognized that by using only routine experimentation it will be possible to define with precision the minimum requirements at both ends of the N-terminal subdomain and the C-terminal subdomain which are necessary to be useful in connection with the present invention.

In order to study the interaction between proteins of interest, one member of the protein pair is fused to the N-terminal subdomain of ubiquitin and the other member of the protein pair is fused to the C-terminal subdomain of ubiquitin. If these proteins (linked to subdomains of ubiquitin) have an affinity for one another, this affinity increases the "effective" (local) concentration of the N-terminal and C-terminal subdomains of ubiquitin, thereby promoting the reconstitution of a quasi-native ubiquitin moiety. For convenience, the term "quasi-native ubiquitin moiety" will be used herein to denote a moiety recognizable as a substrate by ubiquitin-specific proteases. In light of the fact that the N-terminal and C-terminal subdomains of ubiquitin associate to form a quasi-native ubiquitin moiety even in the absence of fusion of the two subdomains to individual members of an interacting protein pair (FIG. 1B), a further requirement is imposed in the present invention in order to increase the resolving capacity of the method for studying such protein interactions. The further requirement is that either the N-terminal subdomain of ubiquitin, or the C-terminal subdomain of ubiquitin, or both, must be mutationally altered to reduce their ability to produce, through their association, a quasi-native ubiquitin moiety. It will be recognized by one of skill in the art that the protein interaction studies described herein are carried out under conditions appropriate for protein/protein interaction. Such conditions are provided in vivo (i.e., under physiological conditions inside living cells) or in vitro, when parameters such as temperature, pH and salt concentration are controlled in a manner intended to mimic physiological conditions.

The mutational alteration of a ubiquitin subdomain is preferably a point mutation. In light of the fact that it is essential that the reconstituted ubiquitin moiety must "look and feel" like native ubiquitin to a ubiquitin-specific protease, mutational alterations which would be expected to grossly affect the structure of the subdomain bearing the mutation are to be avoided. A number of ubiquitin-specific proteases have been reported, and the nucleic acid sequences encoding such proteases are also known (see e.g., Tobias et al., *J. Biol. Chem.* 266:12021 (1991); Baker et al., *J. Biol. Chem.* 267:23364 (1992)). It should be added that all of the at least five ubiquitin-specific proteases in the yeast *S. cerevisiae* require a folded conformation of ubiquitin for its recognition as a substrate. Extensive deletions within the N- or C-terminal subdomains of ubiquitin are an example of the type of mutational alteration which would be expected to grossly affect subdomain structure and, therefore, are examples of types of mutational alterations which should be avoided.

In light of this consideration, the preferred mutational alteration is a mutation in which an amino acid substitution is effected. For example, the substitution of an amino acid having chemical properties similar to the substituted amino acid (e.g., a conservative substitution) is preferred. Specifically, the desired mild perturbation of ubiquitin subdomain interaction is achieved by substituting a chemically similar amino acid residue which differs primarily in the size of its R-group. Such a steric perturbation is expected to introduce a desired (mild) conformational destabilization of a ubiquitin subdomain. The goal is to reduce the affinity of the N-terminal and C-terminal subdomains for one another, not to eliminate this affinity.

In the Exemplification section which follows, the mutational alteration was introduced in the N-terminal subdomain of ubiquitin. More specifically, a first neutral amino acid residue was replaced with a second neutral amino acid having a side chain which differs in size from the first neutral amino acid residue side chain to achieve the desired decrease in affinity. In the Example, the first neutral amino acid residue was isoleucine (either residue 3 or 13 of wild-type ubiquitin). Neutral amino acids which have a side chain which differs in size from isoleucine include glycine, alanine and valine.

A wide variety of fusion construct combinations can be used in the methods of this invention. One strict requirement which applies to all N- and C-terminal fusion construct combinations is that the C-terminal subdomain must bear an amino acid (e.g., peptide, polypeptide or protein) extension. This requirement is based on the fact that the detection of interaction between two proteins of interest linked to two subdomains of ubiquitin is achieved through cleavage after the C-terminal residue of the quasi-native ubiquitin moiety, with the formation of a free reporter protein (or peptide) that had previously been linked to a C-terminal subdomain of ubiquitin. Ubiquitin-specific proteases cleave a linear ubiquitin fusion between the C-terminal residue of ubiquitin and the N-terminal residue of the ubiquitin fusion partner, but they do not cleave an otherwise identical fusion whose ubiquitin moiety is conformationally perturbed. In particular, they do not recognize as a substrate a C-terminal subdomain of ubiquitin linked to a "downstream" reporter sequence, unless this C-terminal subdomain associates with an N-terminal subdomain of ubiquitin to yield a quasi-native ubiquitin moiety.

Furthermore, the characteristics of the C-terminal amino acid extension of the C-terminal ubiquitin subdomain must be such that the products of the cleaved fusion protein are distinguishable from the uncleaved fusion protein. In practice, this is generally accomplished by monitoring a physical property or activity of the C-terminal extension which is cleaved free from the C-terminal ubiquitin moiety. It is generally a property of the free C-terminal extension that is monitored as an indication that a quasi-native ubiquitin has formed, because monitoring of the quasi-native ubiquitin moiety directly is difficult in eukaryotic cells due to the presence of native ubiquitin. While unnecessary for the practice of the present invention, it would of course be appropriate to monitor directly the presence of the quasi-native ubiquitin as well, provided that this monitoring could be carried out in the absence of interference from native ubiquitin (for example, in prokaryotic cells, which naturally lack ubiquitin).

The size of the C-terminal extension which is released following cleavage of the quasi-native ubiquitin moiety within a reporter fusion by a ubiquitin-specific protease is a particularly convenient characteristic in light of the fact that it is relatively easy to monitor changes in size using, for example, electrophoretic methods. For example, if the C-terminal reporter extension has a molecular weight of about 20 kD, the cleavage products will be distinguishable from the non-cleaved quasi-native ubiquitin moiety by virtue of the appearance of a previously absent reporter-specific 20 kD band following cleavage of the reporter fusion.

In light of the fact that the cleavage can take place, for example, in crude cell extracts or in vivo, it is generally not possible to monitor such changes in molecular weight of cleavage products by simply staining an electrophoretogram with a dye that stains proteins nonspecifically, because there are too many proteins in the mixture to analyze in this manner. One preferred method of analysis is immunoblotting. This is a conventional analytical method wherein the cleavage products are separated electrophoretically, generally in a polyacrylamide gel matrix, and subsequently transferred to a charged solid support (e.g., nitrocellulose or a charged nylon membrane). An antibody which binds to the reporter of the ubiquitin-specific protease cleavage products is then employed to detect the transferred cleavage products using routine methods for detection of the bound antibody.

Another useful method is immunoprecipitation of either a reporter-containing fusion to C-terminal subdomains of ubiquitin or the free reporter (liberated through the cleavage by ubiquitin-specific proteases upon reconstitution of a quasi-native ubiquitin moiety) with an antibody to the reporter. The proteins to be immunoprecipitated are first labeled in vivo with a radioactive amino acid such as $^{35}$S-methionine using methods routine in the art. A cell extract is then prepared and reporter-containing proteins are precipitated from the extract using an anti-reporter antibody. The immunoprecipitated proteins are fractionated by electrophoresis in a polyacrylamide gel, followed by detection of radioactive protein species by autoradiography or fluorography.

There are a variety of formats in which these analyses can be carried out. The critical limitation is that the antibody binding pattern to the uncleaved quasi-ubiquitin complex must be distinguishable from the pattern for the cleaved product. For example, the antibody can bind specifically to an epitope of the C-terminal reporter moiety, or it may be a polyclonal antibody preparation specific for the reporter. It is also preferable, for the clearest experimental results (although this is not a strict requirement), that the epitope selected is not one which is native to the system (host cell or extract) in which the experiment is being carried out.

Thus, for example, a preferred experimental design is to extend the C-terminal subdomain of ubiquitin with a peptide containing an epitope foreign to the system in which the assay is being carried out. It is also preferable to design the experiment so that the C-terminal reporter extension of the C-terminal subdomain of ubiquitin is sufficiently large, i.e., easily detectable by the electrophoretic system employed. In this preferred embodiment, the C-terminal reporter extension of the C-terminal subdomain should be viewed as a molecular weight marker. The characteristics of the extension other than its molecular weight and immunological reactivity are not of particular significance. It will be recognized, therefore, that this C-terminal extension can represent an amalgam comprising virtually any amino acid sequence combination fused to an epitope for which a specifically binding antibody is available. This is demonstrated in the Exemplification section wherein the C-terminal extension of the C-terminal ubiquitin subdomain was a combination of the "ha" epitope fused to mouse DHFR (an antibody to the "ha" epitope is readily available).

Aside from the molecular weight of the C-terminal amino acid extension of the C-terminal ubiquitin subdomain, other characteristics can be monitored in order to detect cleavage of a quasi-native ubiquitin moiety. For example, the enzymatic activity of some proteins can be abolished by extending their N-termini. Such a "reporter" enzyme which, in its native form, exhibits an enzymatic activity that is abolished when the enzyme is N-terminally extended, can also serve as the C-terminal reporter linked to the C-terminal ubiquitin subdomain.

In this detection scheme, when the reporter is present as a fusion to the C-terminal ubiquitin subdomain, the reporter protein is inactive. However, if the C-terminal ubiquitin subdomain and the N-terminal ubiquitin subdomain associate to reconstitute a quasi-native ubiquitin moiety in the presence of a ubiquitin-specific protease, the reporter protein will be released, with the concomitant restoration of its enzymatic activity. This method for monitoring cleavage is particularly useful in an in vitro assay for protein interactions. The in vitro assay will be discussed in greater detail below.

The two methods discussed above for monitoring cleavage of the quasi-native ubiquitin moiety are meant to be examples only. Other methods can be devised through the use of routine experimentation.

The quasi-native ubiquitin reconstitution assay for protein interaction can be carried out in a number of formats. Common to such formats is the use of two DNA-based expression constructs. DNA-based expression constructs are genetic elements which can replicate and express the desired proteins within the experimental system employed. The starting material for such expression constructs will typically be a well-characterized expression vector (e.g., a plasmid) which contains regulatory elements (e.g., the origin of replication, promoters, etc.) which are suitable for use within a given experimental system. For example, eukaryotic and prokaryotic expression vectors differ in the types of regulatory sequences which they contain. Many expression vectors suitable for use in a variety of experimental systems have been reported, and are used routinely by those skilled in the art. A review of this fundamental information will not be undertaken here.

The methods of this invention can be used to determine binding between two predetermined proteins, or to determine binding between a predetermined protein and a protein encoded by one or more randomly generated DNA fragments from an organism of interest (library screening method). In the former case, each of the two DNA-based expression constructs is engineered to contain an expression cassette encoding a fusion protein. The first fusion protein comprises an N-terminal ubiquitin subdomain fused to a first protein (say, P1) to be tested for its ability to interact with (i.e., to bind to) a second protein (say, P2). The second fusion protein comprises a C-terminal ubiquitin subdomain fused to P2. In one embodiment of this invention, a C-terminal domain of ubiquitin can be fused to P2 at its N-terminus and to a reporter at its C-terminus. As discussed above, either the N-terminal ubiquitin-subdomain or the C-terminal ubiquitin subdomain, or both are mutationally altered to reduce their ability to associate to form a quasi-native ubiquitin moiety. When the encoded fusion proteins are contacted with one another, binding interaction between P1 and P2 will effectively increase the local concentration of the two ubiquitin subdomains, thereby promoting association and the reconstitution of a quasi-native ubiquitin moiety, which is then cleaved at the junction between the reporter and C-terminal ubiquitin domains by a ubiquitin-specific protease.

The summary description in the preceding paragraph does not discuss certain important experimental considerations. For example, in light of its role as an affinity component, it will be recognized that P1 can be fused to the N-terminus or the C-terminus of the N-terminal ubiquitin subdomain. Similarly, P2 can be fused to the N-terminus or the C-terminus of the C-terminal ubiquitin subdomain. If P2 is fused to the C-terminus of the C-terminal ubiquitin subdomain, it will be removed by cleavage by the ubiquitin-specific protease providing that the ubiquitin subdomains associate to form a quasi-native ubiquitin moiety. Consistent with the summary description in the preceding paragraph, if the P2 moiety is fused to the C-terminus of the C-terminal ubiquitin subdomain, it may also be used as a reporter for detecting reconstitution of a quasi-native ubiquitin moiety. Furthermore, the position of P2 within the C-terminal reporter-containing region of the fusion is not a critical consideration.

The two DNA-based expression constructs can be coexpressed in a host cell known to contain ubiquitin-specific proteases (all eukaryotic cells are known to contain such proteases whose specificity of cleavage is either identical or substantially similar among different species). When maintained under conditions appropriate for metabolic activity, the fusion proteins encoded by both DNA-based expression constructs will be expressed. The cells are subsequently lysed and analyzed for the release of the C-terminal reporter extension of the C-terminal ubiquitin subdomain. This release will occur at significant levels only if P1 and P2 interact under the conditions of the assay.

This coexpression format is carried out, for example in a eukaryotic cell culture (e.g., yeast) which contains a ubiquitin specific protease. Alternatively, the DNA-based expression vectors can be coexpressed in prokaryotic cells (e.g., E. coli) which has been transformed with an expressible gene encoding a ubiquitin-specific protease. Genes encoding ubiquitin-specific proteases have been reported previously, and the introduction of such genes in expressible form into a prokaryotic cell is routine.

An alternative to coexpression of the two DNA-based expression vectors is the expression of the two vectors in different host cell cultures. Extracts from the two cell cultures (or purified, or partially purified preparations of the two fusion proteins) are then combined in presence of a ubiquitin-specific protease. This method permits in vitro analysis of protein interactions. For example, the fusion proteins can be isolated individually, and one can be attached to a solid support (e.g., to a well in a multiwell plate). The second fusion protein is then contacted with the plate-affixed fusion protein in the presence of a ubiquitin-specific protease and, if P1 and P2 bind to one another, the C-terminal reporter extension will be cleaved from the C-terminal ubiquitin subdomain. Whether cleavage has occurred can be determined, for example, by the methods described above. A type of reporter described above, which is enzymatically inactive until its N-terminal extension is cleaved off, can also be used in the in vitro version of this method.

An efficient method for screening for proteins which bind to a protein of interest is the library screening method of the present invention. Like the method described above for studying interactions between two predetermined proteins, the library screening method can be practiced in vivo or in vitro. The library screening method requires the construction of a DNA library in one of the two expression vectors. The source of DNA for the DNA library can be, for example, genomic DNA or cDNA from any organism of interest which has been fragmented to generate DNA fragments of a length appropriate for insertion into a DNA-based expression vector employed.

More specifically, a first protein (P1) is selected for use in a screening procedure designed to identify a second protein (P2) which interacts with P1. A first DNA-based expression vector is provided which contains an expression cassette encoding a C-terminal subdomain of ubiquitin as described above, fused in frame to DNA encoding P1 (and to a reporter moiety if P1 does not double as a reporter). In the fusion protein encoded by the expression cassette, P1 can be fused to either the N-terminus or the C-terminus of the C-terminal ubiquitin subdomain, while a reporter should be fused to the C-terminus of the C-terminal subdomain of ubiquitin.

A second DNA-based expression vector containing an expression cassette is also provided. The second DNA-based expression cassette contains randomly generated DNA fragments (e.g., genomic or cDNA fragments) from an organism of interest fused to DNA encoding the N-terminal subdomain of ubiquitin. In the fusion protein encoded by the expression cassette, any protein (P2) encoded by the randomly generated DNA fragments from the organism of interest can be fused to either the C-terminus or the N-terminus of the N-terminal ubiquitin subdomain. All of the considerations discussed above in connection to the testing of two specific fusion constructs are relevant to all applications of a screen-based version of this method.

It is necessary that the DNA encoding at least one of the two ubiquitin subdomains be mutationally altered to reduce the ability of the encoded N- and C-terminal subdomains of ubiquitin to associate to reconstitute a quasi-native ubiquitin moiety when coexpressed in a cell. The first and second expression vectors are then used to co-transform a suitable host cell.

In the event that the randomly generated DNA from the organism of interest encodes an open reading frame from a protein, it will be expressed as a fusion with the N-terminal ubiquitin subdomain. For purposes of discussion, it will be assumed that the open reading frame encodes a portion of a protein and that in the fusion protein, it is fused to the N-terminus of the N-terminal ubiquitin subdomain.

In the event that proteins P1 and P2 interact with one another, the effective (local) concentration of the N- and C-terminal ubiquitin subdomains will be greatly increased, because they will be brought into mutual proximity through interactions between P1 and P2. This local increase in the concentration of the ubiquitin subdomains promotes the association of the ubiquitin subdomains to reconstitute a quasi-native ubiquitin moiety. This quasi-native ubiquitin moiety is recognized and cleaved by ubiquitin-specific proteases in a cell. The final step in the method is to identify those cells in which the fusion protein encoded by the second DNA-based expression vector is cleaved by ubiquitin-specific proteases. This cleavage is indicative of interaction between P1 and P2, and could be used to locate cells that express a vector encoding a library-derived P2 containing fusion. Cleavage is identified by any of the assays discussed above.

This arrangement can also be reversed. That is, the randomly generated DNA fragment can be fused to the C-terminal ubiquitin subdomain rather than the N-terminal subdomain, and the DNA encoding P1 can be fused to the C-terminal subdomain.

In addition to the in vivo method for screening a DNA expression library, an in vitro method is also disclosed herein. In the practice of the in vitro library screening method, two DNA-based expression vectors are also employed. In order to detect interactions between proteins of interest, constructs similar to those discussed in connection with the in vivo assay are employed. For example, DNA encoding P1 can be fused to DNA encoding the N-terminal ubiquitin subdomain. In the encoded fusion protein, P1 can be fused to either the N-terminus or the C-terminus of the N-terminal ubiquitin subdomain.

The design of the second DNA-based expression vector has limitations which do not apply to the counterpart vector described in connection with the in vivo library screening method. For example, in the in vitro method, the fusion protein encoded by the second DNA-based expression vector is arranged in such a way that P2 is fused to the N-terminus of the C-terminal ubiquitin subdomain. At its C-terminus, the C-terminal subdomain of ubiquitin is fused to a reporter protein which is inactive when N-terminally extended. As in previous applications described Herein, at least one of the ubiquitin subdomains is mutationally altered to reduce the ability of the N- and C-terminal ubiquitin subdomains to associate to reconstitute a quasi-native ubiquitin moiety when contacted under conditions appropriate for protein/protein interactions.

The fusion protein encoded by the first and second expression vectors are then expressed individually in a suitable host, and subsequently purified. It will be recognized, of course, that the cells containing the second DNA-based expression vector must be grown and tested to ensure that a clonal population is being studied. One of the two purified fusion proteins is affixed to a solid support such as wells of a multiwell plate using standard techniques. The other fusion protein is then dissolved in a buffered solution appropriate for protein/protein interactions, and the resulting sample is brought into contact with the protein which is affixed to the solid support. In practice this is accomplished, for example, by placing the suspension in wells in the multiwell plate to which the other fusion protein has already been attached. When incubated under conditions appropriate for protein/protein interactions, the effective local concentration of the N- and C-terminal ubiquitin subdomains will be increased for the reasons discussed previously, providing that P1 and P2 interact with one another. The resulting quasi-native ubiquitin moiety will be recognized by a ubiquitin-specific protease which is added to the incubation mixture and will cleave the complex at the C-terminus of the C-terminal ubiquitin subdomain. This cleavage will activate the reporter protein which is inactive when N-terminally extended. An assay for this newly generated activity is then carried out to determine whether cleavage occurred. Detection of cleavage by this assay is indicative of the interaction between P1 and P2.

When both P1 and P2 are specific, predetermined proteins, this assay can be used as a novel method for analyzing protein/protein interactions in vitro. When P1 (or P2) is a collection of different proteins (analogous to a collection of different DNA fragments encoding different proteins in the in vivo version of the screen described above), the in vitro assay is working as a screen for protein/protein interactions with individual members of the collection of proteins added to specific wells of a multiwell plate to which a fusion containing P2, the C-terminal subdomain of ubiquitin, and a reporter is affixed. Alternatively, individual members of the collection of proteins are affixed to individual wells of a multiwell plate, and a fusion containing P2 and the C-terminal subdomain of ubiquitin is added to the wells in a buffered solution. The multiwell plate-based variants of this in vitro screen are but a few examples of the variants that can readily be devised through the application of only routine experimentation.

Exemplification

In the constructs of this work (FIG. 3), ubiquitin (Ub) was joined to the N-terminus (amino terminus) of the 21-kD mouse dihydrofolate reductase (DHFR). The C-terminus (carboxyl terminus) of DHFR was extended with the "ha" epitope tag, yielding a 22-kD dha (DHFR-ha) reporter. The final constructs resided in the CEN6, TRP-1-based vector pRS314 or in the CEN6, URA3-based pRS316 (Sikorski and Hieter, *Genetics* 122, 19 (1989)), and were expressed from the $P_{CUP1}$ promoter (inserted between the BamHI and EcoRI sites of the pRS314/16 polylinker).

More specifically, the *S. cerevisiae* Ub gene engineered to contain a SalI site immediately upstream of its start codon was amplified, using PCR (see e.g., Ausubel et al., *Current Protocols in Molecular Biology* (Wiley, New York, 1992)), either from the SalI site to the first C of codon 37 or from codon 35 to codon 76. The primers were constructed in a way that yielded, after ligation of the two amplified fragments, a Ub ORF which contained the GGG codon for Gly at position 35 (instead of the synonymous wild-type GGT codon), resulting in a BamHI site between codons 35 and 37. This ORF was ligated to a fragment encoding dha (DHFR-ha) as described by Johnson et al. (*EMBO J.* 11, 497 (1992)), yielding an ORF encoding Ub-dha (FIG. 3-I), which contained the sequence Met-Arg-Ser-Gly-Ile-Met (SEQ ID NO. 4) between Gly$^{76}$ of Ub and Val$^1$ of DHFR.

Fragments encoding Ub mutants (FIG. 3-II, III, IV) were produced by replacing the SalI-BstXI fragment in construct I with double-stranded (ds) oligonucleotides containing a 5' SalI site, a 3' end annealable to the BstXI overhang, and an altered codon at position 13 of Ub. Construct V was produced by replacing residues Ile 3 and Ile 13 of ubiquitin in a Ub-DHFR fusion with Glycine residues. A fragment encoding the i68 insertion (FIG. 3-VI) was produced using PCR, *S. cerevisiae* genomic DNA, and primers designed to amplify the region of STE6 (see e.g., McGrath and Varshavsky, *Nature* 340, 400 (1989); Kuchler et al., *EMBO J.* 8, 3973 (1989)) from codon 196 to codon 262. The primers contained 5' BamHI sites, so that the amplified, BamHI-cut fragment of STE6 could be inserted into the BamHI site between the Ub codons 35 and 37 in constructs I–IV, yielding constructs VI–IX. To avoid a frameshift in the resulting ORFs, the sequence AA was inserted before the STE6 codon 196, resulting in a Glu residue between residue 36 of Ub and residue 196 of Ste6-the first STE6-derived residue of i68. Construct X (FIG. 3) was produced by replacing the SalI-XbaI fragment in construct VI with a ds oligonucleotide that supplied a start codon followed by two Gly codons. In the $C_{ub}$-dha fusion encoded by the resulting fragment (FIG. 3-X), residue 35 of Ub was preceded by a 32-residue linker all of whose residues except the N-terminal Met-Gly-Gly were specified by codons 234 to 262 of STE6.

The $z_1$-$C_{ub}$ portion of construct XV contained the above Ste6-derived sequence preceding the $C_{ub}$ moiety, the leucine zipper region of *S. cerevisiae* GCn4 (see e.g., Vinson et al., *Science* 246, 911 (1989); Hinnebusch, *Proc. Natl. Acad. Sci. USA* 81, 6442 (1984); O'Shea et al., *Science* 254, 539 (1991); Ellenberger et al., *Cell* 71, 1223 (1992); Pu and Struhl, *Nucl. Acids Res.* 21, 4348 (1993)) (residues 235–281, denoted as $z_1$), the construction-generated N-terminal Met, and the sequence Gly-Glu-Ile-Ser-Thr (SEQ ID NO. 5) (FIG. 3-XV). A fragment encoding $z_1$ was produced using PCR, *S. cerevisiae* genomic DNA, and primers that yielded the amplified product bearing single 5' BamHI and SalI sites and single 3' BglII and XbaI sites. Construct XV was produced by replacing the SalI-XbaI fragment of construct VI with the PCR-amplified, SalI/XbaI-cut fragment. To produce constructs XI–XIV, the same fragment was cut with BamHI and XbaI, and was used to replace BamHI-XbaI fragments in derivatives of constructs VI–IX, so that the resulting fragments contained two consecutive stop codons in frame with the $z_1$-coding sequence (codons 235–281 of Gcn4); they also encoded Gly-Glu-Ile-Ser-Thr-Leu-Glu (SEQ ID NO. 6) C-terminally to $z_1$, and Gly-Gly-Ser-Thr-Met (SEQ ID NO. 3) between $z_1$ and $N_{ub}$ (FIG. 3). The $Z_1$ motif in $N_{ub}^{wt}$-$z_1$ and its derivatives but not in $z_1$ $C_{ub}$-dha bore a Met$^{250}$→Thr$^{250}$ replacement (residue numbers of Gcn4), which occured during construction; this replacement would be expected to weaken the interaction between $z_1$ domains. Final DNA constructs were verified by sequencing.

Experiments were carried out to determine whether ubiquitin-specific proteases (UBPs) can cleave a fusion whose Ub moiety bears an insertion within a loop (residues 34–40) connecting the only α-helix of Ub to a β-strand (FIG. 2). The test fusion, Ub$^{i68}$-dha, contained the dha reporter and a 68-residue insertion (denoted as i68) after residue 36 of Ub (FIG. 3-VI). The sequence of the insertion was derived from the cytosolic region of the yeast Ste6 protein between its transmembrane segments 4 and 5 (McGrath and Varshavsky, *Nature* 340, 400 (1989); Kuchler et al., *EMBO J.* 8, 3973 (1989)). This sequence was chosen because it was expected to be either flexible or folded in a way that positions its ends in proximity to each other.

*S. cerevisiae* expressing Ub-dha or Ub$^{i68}$-dha (FIG. 3-I, VI) were labeled with $^{35}$S-methionine for 2 or 5 min at 30° C. Whole cell extracts (prepared in the presence of N-ethylmaleimide to inhibit UBPs) were incubated with anti-ha antibody, and immunoprecipitated proteins were analyzed by SDS-PAGE. All experiments used the YPH500 strain of *S. cerevisiae* (MATa ura3 lys2 trp1 ade2 his3 leu2) grown at 30° C. to $A_{600}$ of ~1 in a synthetic (SD) medium containing 0.1 mM CuSO$_4$. Transformation of *S. cerevisiae*, labeling with $^{35}$S-methionine, cold chase, preparation of whole cell extracts in the presence of N-ethylmaleimide, immunoprecipitation with a monoclonal anti-ha antibody, SDS-PAGE (12%) and fluorography were carried out as described by Johnson et al. (*EMBO J.* 11, 497 (1992)), except that "zero" time samples were withdrawn and processed 1 min (at 30° C.) after the addition of a chase medium containing cycloheximide and unlabeled methionine. The labeling time was either 2 or 5 min, as indicated. Immunoblot analysis with anti-ha antibody was performed as described, except that the ECL detection system (Amersham) was used.

The in vivo cleavage of Ub-dha and Ub$^{i68}$-dha was complete by the end of a 2-min pulse. Thus, a large insertion within the 34–40 region of Ub (FIGS. 1A and 2) does not interfere with the recognition of Ub by UBPs, suggesting that at least within the limits of temporal resolution of the 2-min pulse-cleavage assay, this insertion does not perturb the folding of Ub.

A fusion whose Ub moiety bears replacements of Ile$^3$ and Ile$^{13}$ with Gly residues is cleaved in vivo much more slowly than an otherwise identical fusion bearing wild-type Ub. Since Ile$^3$ and Ile$^{13}$ are buried in the hydrophobic core of Ub (Vijay-Kumar et al., *J. Mol. Biol.* 194, 531 (1987)), their conversion to glycines is expected to decrease the conformational stability of Ub without necessarily changing its overall folding pattern. To make similar but less destabilizing alterations in the sequence of Ub, only Ile$^{13}$ was replaced with either Val, Ala or Gly hydrophobic residues of decreasing size. The resulting Ub fusions, Ub$^{V13}$-dha, Ub$^{A13}$-dha, and Ub$^{G13}$-dha (FIG. 3-II, III, IV), were completely cleaved by the end of a 5-min pulse, as was also Ub-dha, bearing wild-type Ub.

A combination of the i68 insertion (FIG. 2) and a substitution at position 13 of Ub was then tested to determine whether such a combination results in a less efficient cleavage of a fusion by UBPs. By the end of a 2-min pulse, no uncleaved Ub$^{i68}$-dha, and at most traces of Ub$^{V13,i68}$-dha could be detected. However, the cleavage of Ub$^{A13,i68}$-dha, and especially of Ub$^{G13,i68}$-dha was much slower, in that significant amounts of the uncleaved fusions were observed by the end of a 2-min pulse (FIGS. 3-VIII, IX and 4B, lanes c and d).

The i68 insertion places the two "halves" of a nascent Ub farther apart (FIGS. 1A and 2), and therefore is expected to retard the folding of Ub; this effect was not detected apparently because of insufficient temporal resolution of the 2-min pulse-cleavage assay. However, the assay did detect a decrease in the rate of Ub folding with fusions whose Ub moieties bear both the insertion and another alteration such as Ile$^{13}\rightarrow$Gly$^{13}$, which by itself is also insufficient to cause a detectable retardation of Ub folding. These results can be interpreted within the diffusion-collision model of protein folding (Karplus and Weaver, *Nature* 260, 404 (1976); Kim and Baldwin, *Annu. Rev. Biochem.* 51, 459 (1982); Jaenicke, *Biochemistry* 30, 3147 (1991)), in which marginally stable units of isolated secondary structure form early and then coalesce into the native conformation, with the overall rate of folding dependent on both the stability of folded subdomains and on the rates of their collision and coalescence. In this view, the relevant subdomains of Ub are its N-terminal and C-terminal regions (residues 1 to ~36 and ~37 to 76, respectively). Indeed, in the native Ub, its first 34 residues are folded into an e-helix interacting with a double-stranded antiparallel β-sheet (FIG. 2) (Vijay-Kumar et al., *J. Mol. Biol.* 194, 531 (1987)). Thus, the i68 insertion retards Ub folding primarily through a reduction in the frequency of collisions between the N-terminal and C-terminal subdomains of Ub, whereas the effect of substitutions at position 13 is a decreased conformational stability of the N-terminal subdomain, caused by disruption of contacts between Ile$^{13}$ in the second strand of the β-sheet and the hydrophobic face of the α-helix (FIG. 2).

The finding that $N_{ub}$ and $C_{ub}$ fragments of ubiquitin are its conformational subdomains is also supported by a spectroscopic study of the chemically synthesized halves of ubiquitin, in which it was found that fragments closely related to the $N_{ub}$ and $C_{ub}$ as disclosed herein are largely unfolded in an aqueous buffer but display spectroscopic properties indicative of partial folding in the presence of 20% methanol (a secondary structure-stabilizing solvent) (see Cox et al., *J. Mol. Biol.* 234:483 (1993)).

The relative insensitivity of Ub folding to a large insertion within the 34–40 loop (FIGS. 1A and 2) suggested that separate, coexpressed N-terminal and C-terminal fragments of Ub might also be able to reconstitute the folded Ub conformation detectable by the UBP cleavage assay. In a test of this conjecture, a C-terminal fragment of wild-type Ub (residues 35–76, denoted as $C_{ub}$) was expressed as a fusion to the dha reporter ($C_{ub}$-dha), while an N-terminal fragment of wild-type Ub (residues 1–37, denoted as $N_{ub}^{wt}$) was expressed as a fusion to the "leucine zipper" homodimerization domain of the yeast Gcn4 protein ($N_{ub}^{wt}$-$z_1$, with $z_1$ denoting the zipper of Gcn4) (FIG. 3-X, XI).

*S. cerevisiae* expressing $C_{ub}$-dha either alone or together with $N_{ub}^{wt}$-$z_1$ were labeled with $^{35}$S-methionine for 5 min at 30° C., followed by a chase for 0, 10 and 30 min, and SDS-PAGE analysis of labeled proteins immunoprecipitated with anti-ha antibody. When expressed by itself, $C_{ub}$-dha remained uncleaved at the junction between $C_{ub}$ and dha; instead, the entire fusion was slowly degraded. However, coexpression of $C_{ub}$-dha and $N_{ub}^{wt}$-$z_1$ resulted in the cleavage of $C_{ub}$-dha, yielding the long-lived dha reporter which accumulated during a 30-min chase. This cleavage was slow in comparison to the cleavage of otherwise identical fusions containing either the wild-type or the insertion-bearing Ub moiety; the latter cleavages were complete by the end of a 2-min pulse.

It can be concluded from this data that the cleavage of $C_{ub}$-dha requires the presence of $N_{ub}^{wt}$-$z_1$, and is the consequence of an in vivo association between the $C_{ub}$ and $N_{ub}^{wt}$ moieties of these fusions. This association results in at least transient formation of a Ub moiety which is similar enough to native Ub to be a substrate of UBPs. The relatively low overall rate of the $C_{ub}$-dha cleavage apparently results from a low overall rate of "productive" in vivo collisions between the $C_{ub}$ and $N_{ub}^{wt}$ fragments, in comparison to the rate of analogous collisions between the same subdomains of Ub when they are linked within a single polypeptide (FIG. 1A, B). In other words, the effective (local) concentration of the two Ub subdomains is much higher for linked than for unlinked subdomains.

The efficiency of reconstitution of native Ub from its coexpressed subdomains depended on conformational stability of the N-terminal subdomain: coexpression of $C_{ub}$-dha (FIG. 3-X) with either $N_{ub}^{13}$-$z_1$ or $N_{ub}^{13}$-$z_1$ (FIG. 3-XIII, XIV), which bore Gly or Ala instead of wild-type Ile at position 13, resulted in virtually no cleavage of $C_{ub}$-dha, in contrast to the results with either $N_{ub}^{wt}$-$z_1$ or $N_{ub}^{V13}$-$z_1$ (FIG. 3-XI, XII), which bore either Ile, the wild-type residue, or Val, a hydrophobic residue larger than Ala and Gly, at position 13 (FIG. 1C).

To analyze a conformationally destabilized Ub, it was determined whether the folding of a Ub moiety containing an altered subdomain could be "rescued" in trans by the wild-type version of the same subdomain. Ub$^{G3,13}$-dha (FIG. 3-V), whose Ub moiety bears conformationally destabilizing replacements of Ile$^3$ and Ile$^{13}$ with Gly residues, is cleaved in vivo very slowly: whereas the cleavage of Ub-dha was complete by the end of a 5-min or even a 2-min pulse, only ~10% of Ub$^{G3,13}$-dha was cleaved by the end of a 5-min pulse, and ~33% was cleaved after a 10-min chase. However, coexpression of Ub$^{G3,13}$-dha and $N_{ub}^{wt}$-$z_1$ (FIG. 3-XI) increased the yield of cleaved Ub$^{G3,13}$-dha (after 10 min of chase) from ~33% to ~66%. Significantly, this rate of cleavage was still lower than that observed with coexpressed $N_{ub}^{wt}$-$z_1$ and $C_{ub}$-dha, when Ub reconstitution could occur exclusively in trans (FIG. 1A).

Thus, although $Ub^{G3,13}$ is able to adopt a quasi-native (recognizable by UBPs) Ub conformation, the altered N-terminal subdomain of $Ub^{G3,13}$ also impedes the association between the $C_{ub}$ subdomain of $Ub^{G3,13}$ and the coexpressed, trans-acting $N_{wt}^{ub}$ subdomain. A model that accounts for these findings posits two ensembles of the conformationally unstable $Ub^{G3,13}$ moieties: (i) a set of "open" or "unfolded" $Ub^{G}3,13$ conformations which allow the "invasion" by the coexpressed $N_{ub}^{wt}$ fragment and its coalescence with the $C_{ub}$ region of $Ub^{G3,13}$-dha, resulting in reconstitution of Ub moiety and in the fusion's cleavage; (ii) a set of "closed" or "folded" $Ub^{G3,13}$ conformations which preclude the invasion by $N_{ub}^{wt}$. These conformations, in addition to interconverting with open conformations, include quasi-native Ub species that can be recognized by UBPs.

That fragments of a protein can reassociate to form a functional, quasi-native species has been demonstrated for a variety of proteins other than Ub; the examples include ribonuclease A, staphylococcal nuclease and other proteins in vitro (Anfinsen et al., *Enzymes* 4, 177 (1971); Hantgan and Taniuchi, *J. Biol. Chem.* 252, 1367 (1977); Holmgren and Slaby, *Biochemistry* 18, 5591 (1979); Galakatos and Walsh, *Biochemistry* 26, 8475 (1987); Girons et al., *J. Biol. Chem.* 262, 622 (1987); Johnsson and Weber, *Eur. J. Biochem.* 1 (1990)), and also *S. cerevisiae* isoleucyl-tRNA synthetase, *E. coli* Lac permease and Tet protein in vivo (Landro and Schimmel, *Curr. Op. Str. Biol.* 3, 549 (1993); Shiba and Schimmel, *Proc. Natl. Acad. Sci. USA* 89, 1880 (1992); Rubin and Levy, *J. Bact.* 173, 4503 (1991); Wrubel et al., *J. Bact.* 172, 5374 (1990); Bibi and Kaback, *Proc. Natl. Acad. Sci. USA* 87, 4325 (1990)). A previously unexplored aspect of protein reconstitution was the finding by the present inventors that alterations in conformational stability of Ub fragments strongly influence the efficiency of Ub reassembly. This result, together with the discovery that the UBP-mediated cleavage of a Ub fusion requires folded Ub, led the inventors to a new assay for in vivo protein interactions, as shown below.

Experiments were designed to determine whether linking of two polypeptides that interact in vivo to $N_{ub}$ and $C_{ub}$ could facilitate reconstitution of Ub by bringing the Ub fragments close together. The $C_{ub}$-dha fusion was linked to a region of *S. cerevisiae* Gcn4 (residues 235–281) that contained the extensively characterized leucine zipper homodimerization domain (denoted as $z_1$) but lacked an essential part of the Gcn4 DNA-binding domain (Vinson et al., *Science* 246, 911 (1989); Hinnebusch, *Proc. Natl. Acad. Sci. USA* 81, 6442 (1984); O'Shea et al., *Science* 254, 539 (1991); Ellenberger et al., *Cell* 71, 1223 (1992); Pu and Struhl, *Nucl. Acids Res.* 21, 4348 (1993)). In the resulting $z_1C_{ub}$-dha, a 32-residue linker, derived from the yeast Ste6 sequence, was inserted between the $z_1$ zipper and $C_{ub}$ (FIG. 3-XV) to ensure that $N_{ub}$ and $C_{ub}$ subdomains could be spatially proximal within a $z_1$-mediated complex between $z_1C_{ub}$-dha and $N_{ub}$-$z_1$.

When expressed by itself, $z_1C_{ub}$-dha remained uncleaved at the $C_{ub}$-dha junction, and was slowly degraded during the chase, similarly to the results with $C_{ub}$-dha, which lacked $z_1$. However, coexpression of $z_1C_{ub}$-dha and $N_{ub}^{G13}$-$z_1$, bearing a destabilizing Ile→Gly replacement at position 13 of Ub, resulted in a significant cleavage of $z_1C_{ub}$-dha (yielding dha) in the course of a 30-min chase (FIGS. 3-XIV and XV). In contrast, no such cleavage was observed when $N_{ub}^{G13}$-$z_1$ was coexpressed with $C_{ub}$-dha, which lacked the $z_1$ dimerization domain.

Similar results (but with a faster cleavage of $z_1C_{ub}$-dha) were obtained upon coexpression of $z_1C_{ub}$-dha and $N_{ub}^{A13}$-$z_1$, which bore Ala instead of wild-type Ile at position 13 of Ub. Moreover, the enhancement of Ub reassembly by $z_1$—$z_1$ interactions was observed even with pairs of Ub fragments that could reconstitute Ub by themselves (in the absence of linked $z_1$). Specifically, whereas coexpression of $C_{ub}$-dha and $N_{ub}^{wt}$-$z_1$ or $N_{ub}^{V13}$-$z_1$ resulted in detectable but slow cleavage of $C_{ub}$-dha that was still incomplete after 30 min of chase, coexpression of $z_1C_{ub}$-dha and $N_{ub}^{wt}$-$z_1$ or $N_{ub}$-$z_1$ resulted in the nearly complete cleavage of $z_1C_{ub}$-dha (yielding dha) by the end of a 5-min pulse.

The temporal resolution of this assay could be increased by shortening the labeling time from 5 to 2 min. For example, the amounts of $z_1C_{ub}$-dha cleaved by the end of a 2-min pulse progressively increased when $z_1C_{ub}$-dha was coexpressed, respectively, with $N_{ub}^{G13}$-$z_1$, $N_{ub}^{A13}$-$z_1$, and $N_{ub}^{V13}$-$z_1$. By contrast, no cleavage of $z_1C_{ub}$-dha was observed when it was expressed by itself, or when $N_{ub}^{A13}$-$z_1$ or $N_{ub}^{G13}$-$z_1$ were coexpressed with $C_{ub}$-dha, which lacked the $z_1$ zipper.

To determine steady-state levels of ha-containing test proteins, whole cell extracts were fractionated by SDS-PAGE and analyzed by immunoblotting with anti-ha antibody. When $C_{ub}$-dha was expressed in the absence of the N-terminal Ub fragment, the bulk of $C_{ub}$-dha remained uncleaved. When $N_{ub}^{A13}$-$z_1$ was coexpressed with $C_{ub}$-dha, a fraction of $C_{ub}$-dha was cleaved to yield dha. However, when $N_{ub}^{A13}$-$z_1$ was coexpressed with $z_1C_{ub}$-dha, virtually all of $z_1C_{ub}$-dha was cleaved to yield dha. Similar results were obtained with $N_{ub}^{A13}$-$z_1$, but the "signal-to-noise" ratio was lower, in that a significant fraction of $z_1C_{ub}$-dha remained uncleaved in the presence of $N_{ub}^{G13}$-$z_1$, whereas virtually all of $z_1C_{ub}$-dha was cleaved in the presence of $N_{ub}^{A13}$-$z_1$.

Thus, selecting appropriate Ub fragments, altering at least one of them to reduce the rate of Ub reconstitution by fragments alone, and linking these fragments to a pair of test polypeptides resulted in a ubiquitin-based split-protein sensor, or USPS-a new type of in vivo assay for kinetic and equilibrium aspects of protein interactions.

USPS differs qualitatively from a recent approach, the two-hybrid technique (Fields and Song, *Nature* 340:245 (1989); Chien et al., *Proc. Natl. Acad. Sci. USA* 88:9578 (1991); Guarante, *Trends Genet.* 90:1639 (1993); Gyuris et al., *Cell* 75:791 (1993)), which is based on expressing one protein as a fusion to a DNA-binding domain of a transcriptional activator, and expressing another protein as a fusion to a transcriptional activation domain. If the test proteins interact in vivo, a transcriptional activator is reconstituted, resulting in the induction of a reporter gene. Reconstitution of a transcriptional activator in the two-hybrid technique involves the generation of proximity between two conformationally independent protein domains whose functions do not depend on direct contacts between the domains.

By contrast, USPS involves the spatial (conformational) reconstitution of a single-domain protein from its conformationally unstable subdomains, which acquire an assayable function as a result of their direct physical contact and stabilization of their conformations. Also in contrast to the USPS method, the two-hybrid technique cannot address temporal aspects of a protein-protein interaction. In addition, the two-hybrid technique limits the set of detectable protein interactions to those that occur (or can be "reproduced") in the nucleus, in proximity to the reporter gene. By contrast, the USPS method makes possible the detection and monitoring of a protein-protein interaction as a function of time, at the natural sites of this interaction in a living cell.

USPS was demonstrated here with homodimerizing polypeptides of the leucine zipper type. In addition, USPS was used to detect and analyze in vivo interactions between S. cerevisiae Sec62, an integral membrane protein, and the signal sequences of either the SUC2-encoded invertase or the MFα1-encoded precursor of α-factor, a mating pheromone. The USPS assay detected specific, transient interactions between Sec62 and the above signal sequences; it also made possible a kinetic dissection of these interactions, which have previously been demonstrated in a cell-free system but not in vivo.

---

We claim:

1. A fusion protein comprising an N-terminal subdomain of ubiquitin, fused to a non-ubiquitin protein or peptide, the N-terminal subdomain of ubiquitin being mutationally altered to reduce its ability to associate with a C-terminal subdomain of ubiquitin, thereby reconstituting a quasi-native ubiquitin moiety, when contacted with a C-terminal subdomain of ubiquitin under conditions appropriate for protein/protein interaction, the N-terminal subdomain being mutationally altered by replacing a first hydrophobic contact residue with a second hydrophobic contact residue having a side chain which differs in size from the first hydrophobic contact residue side chain.

2. The fusion protein of claim 1, wherein the first amino acid residue is isoleucine.

3. The fusion protein of claim 2, wherein the isoleucine is either isoleucine 3, or isoleucine 13 of wild-type ubiquitin.

4. The fusion protein of claim 3, wherein the isoleucine 3 or isoleucine 13 is replaced with an amino acid residue selected from the group consisting of glycine, alanine, valine or leucine.

5. A fusion protein comprising a C-terminal subdomain of ubiquitin, fused to the N-terminus of a non-ubiquitin protein or peptide, the fusion protein being cleavable by a ubiquitin-specific protease under conditions wherein the C-terminal subdomain of ubiquitin associates with an N-terminal subdomain of ubiquitin to form a quasi-native ubiquitin moiety, the products of the cleaved fusion protein being distinguishable from the uncleaved fusion protein.

6. The fusion protein of claim 5 further comprising an N-terminal protein or peptide extension of the ubiquitin subdomain.

7. The fusion protein of claim 5 wherein the non-ubiquitin protein or peptide contains, or is attached to an epitope recognized by an antibody, thereby facilitating immunological detection or isolation of the fusion protein or, following the cleavage of the fusion protein by a ubiquitin-specific protease, facilitates the immunological detection or isolation of the subdomain of the fusion protein located C-terminally relative to the C-terminal ubiquitin subdomain in the uncleaved fusion protein.

8. The fusion protein of claim 7 further comprising an N-terminal protein or peptide extension of the ubiquitin subdomain.

9. A DNA-based expression vector containing an expression cassette encoding a fusion protein comprising a C-terminal subdomain of ubiquitin, fused to the N-terminus of a non-ubiquitin protein or peptide, the fusion protein being cleavable by a ubiquitin-specific protease under conditions wherein the C-terminal subdomain of ubiquitin associates with an N-terminal subdomain of ubiquitin to form a quasi-native ubiquitin moiety, the products of the cleaved fusion protein being distinguishable from the uncleaved fusion protein.

10. A DNA expression library comprising a DNA-based expression vector containing an expression cassette comprising DNA encoding an N-terminal subdomain of ubiquitin, fused to termini of DNA fragments from an organism of interest, DNA encoding a hydrophobic contact residue of the N-terminal subdomain of ubiquitin being mutationally altered to encode an N-terminal subdomain of ubiquitin having reduced ability to associate with a C-terminal subdomain of ubiquitin to reconstitute a quasi-native ubiquitin moiety when contacted with a C-terminal subdomain of ubiquitin under conditions appropriate for protein/protein interaction, the DNA encoding the hydrophobic contact residue being mutationally altered to encode a second hydrophobic contact residue having a side chain which differs in size from the first hydrophobic contact residue side chain.

11. A DNA expression library comprising a DNA-based expression vector containing an expression cassette comprising DNA encoding a C-terminal subdomain of ubiquitin fused to termini of a DNA fragment of an organism of interest, the fusion protein encoded by the expression cassette comprising the C-terminal subdomain of ubiquitin fused to the N-terminus of a polypeptide encoded by the DNA fragment of the organism of interest, the fusion protein being cleavable by a ubiquitin-specific protease under conditions wherein the C-terminal subdomain of ubiquitin associates with an N-terminal subdomain of ubiquitin to form a quasi-native ubiquitin moiety, the products of the cleaved fusion protein being distinguishable from the uncleaved fusion protein.

12. A method for identifying interacting proteins or peptides, comprising:
  a) providing a first DNA-based expression vector containing an expression cassette encoding an N-terminal subdomain of ubiquitin fused to DNA encoding a first protein or peptide; and providing a second DNA-based expression vector containing an expression cassette encoding a C-terminal subdomain of ubiquitin fused to randomly generated DNA fragments produced by cleaving cDNA from an organism of interest, the encoded fusion protein being cleavable by a ubiquitin-specific protease under conditions wherein the C-terminal subdomain of ubiquitin associates with an N-terminal subdomain of ubiquitin to form a quasi-native ubiquitin moiety; a hydrophobic contact residue encoded by the first DNA sequence being mutationally altered to reduce the ability of the encoded N- and C-terminal subdomains of ubiquitin to associate to reconstitute a quasi-native ubiquitin moiety when coexpressed in a cell, the DNA encoding the hydrophobic contact residue being mutationally altered to encode a second hydrophobic contact residue having a side chain which differs in size from the first hydrophobic contact residue side chain;
  b) co-transforming a cell with the first DNA-based expression vector and the second DNA-based expression vector; and
  c) detecting cells in which the fusion protein encoded by the second DNA-based expression vector is cleaved by a ubiquitin-specific protease, the cleavage being indicative of interaction between the first protein or peptide and a second protein or peptide encoded by the randomly generated DNA from an organism of interest.

13. A method for identifying interacting proteins or peptides, comprising:
  a) providing a first DNA-based expression vector containing an expression cassette encoding an N-terminal subdomain of ubiquitin fused to a randomly generated DNA fragment from an organism of interest; providing a second DNA-based expression vector encoding a C-terminal subdomain of ubiquitin fused to DNA encoding a first protein or peptide, the encoded fusion protein being cleavable by a ubiquitin-specific protease under conditions wherein the C-terminal subdomain of ubiquitin associates with an N-terminal subdomain of ubiquitin to form a quasi-native ubiquitin moiety; a hydrophobic contact residue encoded by the first DNA sequence being mutationally altered to reduce the ability of the encoded N- and C-terminal subdomains to associate to reconstitute a quasi-native ubiquitin moiety when coexpressed in a cell, the DNA encoding the hydrophobic contact residue being mutationally altered to encode a second hydrophobic contact residue having a side chain which differs in size from the first hydrophobic contact residue side chain;
  b) co-transforming a cell with the first DNA-based expression vector and the second DNA-based expression vector; and
  c) detecting cells in which the fusion protein encoded by the second DNA-based expression vector is cleaved by a ubiquitin-specific protease, the cleavage being indicative of interaction between the first protein or peptide and a second protein or peptide encoded by the the randomly generated DNA fragment from the organism of interest.

14. A method for identifying interacting proteins or peptides, comprising:
  a) providing a first fusion protein comprising an N-terminal subdomain of ubiquitin fused to a first protein or peptide; providing a second fusion protein comprising a C-terminal subdomain of ubiquitin fused at its N-terminus to a second protein or peptide and fused at its C-terminus to a reporter protein which is inactive when N-terminally extended, the second fusion protein being cleavable by a ubiquitin-specific protease under conditions wherein the C-terminal subdomain of ubiquitin associates with an N-terminal subdomain of ubiquitin to form a quasi-native ubiquitin moiety; a hydrophobic contact residue of the N-terminal subdomain of ubiquitin being mutationally altered to reduce the ability of the N- and C-terminal subdomains to associate to reconstitute a quasi-native ubiquitin moiety when contacted under conditions appropriate for protein/protein interaction the hydrophobic contact residue being mutationally altered to encode a second hydrophobic contact residue having a side chain which differs in size from the first hydrophobic contact residue side chain;

b) fixing either the first fusion protein or the second fusion protein to a solid support thereby creating a fixed fusion protein;

c) contacting the fixed fusion protein with a solution containing a fusion protein selected from the group consisting of the first fusion protein or the second fusion protein under conditions appropriate for protein/protein interaction, the fusion protein in solution being the fusion protein which was not fixed to the solid support in step b);

d) contacting a quasi-native ubiquitin complex formed in step c) with a ubiquitin-specific protease under conditions appropriate for protease activity; and e) detecting cleavage of the quasi-native ubiquitin complex by assaying for activity of the reporter protein which is active following cleavage which removes its N-terminal extension, the cleavage being indicative of protein interaction.

15. A method for identifying interacting proteins or peptides, comprising:

a) providing a first DNA-based expression vector containing an expression cassette containing a first DNA sequence encoding an N-terminal subdomain of ubiquitin fused to DNA encoding a first protein or peptide; and providing a second DNA-based expression vector containing an expression cassette containing a second DNA sequence encoding a C-terminal subdomain of ubiquitin fused at its N-terminus to randomly generated DNA fragments produced by cleaving DNA from an organism of interest, and fused at its C-terminus to a reporter protein which is inactive when N-terminally extended, the encoded fusion protein being cleavable by a ubiquitin-specific protease under conditions wherein the C-terminal subdomain of ubiquitin associates with an N-terminal subdomain of ubiquitin to form a quasi-native ubiquitin moiety; a hydrophobic contact residue encoded by the first DNA sequence being mutationally altered to reduce the ability of the encoded N- and C-terminal subdomains of ubiquitin to associate to reconstitute a quasi-native ubiquitin, the DNA encoding the hydrophobic contact residue being mutationally altered to encode a second hydrophobic contact residue having a side chain which differs in size from the first hydrophobic contact residue side chain;

b) expressing the fusion proteins encoded by the first and second DNA-based expression vectors, either together or independently, in a cell which does not contain a ubiquitin-specific protease;

c) purifying the fusion protein encoded by the first DNA-based expression vector;

d) affixing the purified fusion protein to a solid support, thereby creating a fixed fusion protein;

e) contacting the fixed fusion protein with a solution containing the fusion protein encoded by the second DNA-based expression vector, under conditions appropriate for protein/protein interaction;

f) contacting a quasi-native ubiquitin complex formed in step e) with a ubiquitin-specific protease under conditions appropriate for protease activity; and g) detecting cleavage of the quasi-native ubiquitin complex by assaying for activity of the reporter protein which is active following cleavage which removes its N-terminal extension, the cleavage being indicative of protein interaction.

16. A method for identifying interacting proteins or peptides, comprising:

a) providing a first DNA-based expression vector containing an expression cassette containing a first DNA sequence encoding an N-terminal subdomain of ubiquitin fused to randomly generated DNA fragments produced by cleaving DNA from an organism of interest; and providing a second DNA-based expression vector containing an expression cassette containing a second DNA sequence encoding a C-terminal subdomain of ubiquitin fused at its N-terminus to a second protein or peptide and fused at its C-terminus to a reporter protein which is inactive when N-terminally extended, the encoded fusion protein being cleavable by a ubiquitin-specific protease under conditions wherein the C-terminal subdomain of ubiquitin associates with an N-terminal subdomain of ubiquitin to form a quasi-native ubiquitin moiety; a hydrophobic contact residue encoded by the first DNA sequence being mutationally altered to reduce the ability of the encoded N- and C-terminal subdomains of ubiquitin to associate to reconstitute a quasi-native ubiquitin moiety, the DNA encoding the hydrophobic contact residue being mutationally altered to encode a second hydrophobic contact residue having a side chain which differs in size from the first hydrophobic contact residue side chain;

b) expressing the fusion proteins encoded by the first and second DNA-based expression vectors, either together or independently, in a cell which does not contain a ubiquitin-specific protease;

c) purifying the fusion protein encoded by the second DNA-based expression vector;

d) affixing the purified fusion protein from step c) to a solid support thereby creating a fixed fusion protein;

e) contacting the fixed fusion protein with a solution containing the fusion protein encoded by the first DNA-based expression vector, under conditions appropriate for protein/protein interaction;

f) contacting a quasi-native ubiquitin complex formed in step e) with a ubiquitin-specific protease under conditions appropriate for protease activity; and g) detecting cleavage of the quasi-native ubiquitin complex by assaying for activity of the reporter protein which is active following cleavage which removes its N-terminal extension, the cleavage being indicative of protein interaction.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 228 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..228

( x i ) SEQUENCE DESCRIPTION: SEQ ID NO:1:

```
ATG  CAA  ATT  TTC  GTC  AAG  ACT  TTA  ACC  GGT  AAG  ACT  ATT  ACC  CTG  GAA      48
Met  Gln  Ile  Phe  Val  Lys  Thr  Leu  Thr  Gly  Lys  Thr  Ile  Thr  Leu  Glu
 1                    5                   10                   15

GTT  GAA  TCT  TCT  GAC  ACT  ATT  GAC  AAT  GTC  AAG  TCC  AAG  ATC  CAA  GAC      96
Val  Glu  Ser  Ser  Asp  Thr  Ile  Asp  Asn  Val  Lys  Ser  Lys  Ile  Gln  Asp
                20                        25                        30

AAG  GAA  GGT  ATT  CCA  CCT  GAC  CAA  CAA  AGA  TTG  ATC  TTT  GCT  GGT  AAG     144
Lys  Glu  Gly  Ile  Pro  Pro  Asp  Gln  Gln  Arg  Leu  Ile  Phe  Ala  Gly  Lys
           35                        40                        45

CAA  TTG  GAA  GAT  GGT  AGA  ACT  TTG  TCC  GAC  TAC  AAC  ATC  CAA  AAG  GAA     192
Gln  Leu  Glu  Asp  Gly  Arg  Thr  Leu  Ser  Asp  Tyr  Asn  Ile  Gln  Lys  Glu
     50                        55                        60

TCT  ACT  CTA  CAC  TTG  GTC  TTG  AGA  TTG  AGA  GGT  GGT                         228
Ser  Thr  Leu  His  Leu  Val  Leu  Arg  Leu  Arg  Gly  Gly
 65                    70                        75
```

( 2 ) INFORMATION FOR SEQ ID NO:2:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gln  Ile  Phe  Val  Lys  Thr  Leu  Thr  Gly  Lys  Thr  Ile  Thr  Leu  Glu
 1                    5                   10                   15

Val  Glu  Ser  Ser  Asp  Thr  Ile  Asp  Asn  Val  Lys  Ser  Lys  Ile  Gln  Asp
                20                        25                        30

Lys  Glu  Gly  Ile  Pro  Pro  Asp  Gln  Gln  Arg  Leu  Ile  Phe  Ala  Gly  Lys
           35                        40                        45

Gln  Leu  Glu  Asp  Gly  Arg  Thr  Leu  Ser  Asp  Tyr  Asn  Ile  Gln  Lys  Glu
     50                        55                        60

Ser  Thr  Leu  His  Leu  Val  Leu  Arg  Leu  Arg  Gly  Gly
 65                    70                        75
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly  Gly  Ser  Thr  Met
 1                    5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Met  Arg  Ser  Gly  Ile  Met
 1                    5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Gly  Glu  Ile  Ser  Thr
 1                    5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Gly  Glu  Ile  Ser  Thr  Leu  Glu
 1                    5
```